United States Patent [19]

Lachocki et al.

[11] Patent Number: 5,648,314
[45] Date of Patent: Jul. 15, 1997

[54] SLOW-DISSOLVING MULTI-FUNCTIONAL SANITIZER AND CLARIFIER

[75] Inventors: Thomas M. Lachocki, Duluth; Oscar T. Ragin, Stone Mountain; Presley K. Mitchell, Marietta, all of Ga.

[73] Assignee: Bio-Lab, Inc., Decatur, Ga.

[21] Appl. No.: 441,384

[22] Filed: May 15, 1995

[51] Int. Cl.$^6$ .................. A01N 59/00; A01N 59/06; A01N 59/14; A01N 43/66
[52] U.S. Cl. .......... 504/151; 504/152; 504/155; 504/156; 424/405; 424/408; 424/409; 424/657; 424/658; 424/659; 424/660; 424/661; 424/667; 424/673; 424/682; 424/698; 514/241; 514/258; 514/387; 514/389; 210/753; 210/754; 210/755; 210/756
[58] Field of Search ................ 504/151, 152, 504/155, 156; 424/660, 657, 698, 405, 408, 409, 658, 659, 661, 667, 673, 682; 514/241, 387, 258, 389; 210/754, 755, 756, 753

[56] References Cited

U.S. PATENT DOCUMENTS

| | | | |
|---|---|---|---|
| 4,043,931 | 8/1977 | Jeffrey et al. | 252/93 |
| 4,350,666 | 9/1982 | Klutts | 422/263 |
| 4,460,490 | 7/1984 | Barford et al. | 252/92 |
| 4,594,091 | 6/1986 | Girvan | 71/67 |
| 4,738,728 | 4/1988 | Barford et al. | 134/34 |
| 5,015,643 | 5/1991 | Jones et al. | 514/241 |
| 5,021,186 | 6/1991 | Ota et al. | 252/186.35 |
| 5,178,787 | 1/1993 | Hung et al. | 252/90 |
| 5,205,955 | 4/1993 | Bunczk et al. | 252/102 |
| 5,330,676 | 7/1994 | Glen | 252/186.35 |
| 5,338,461 | 8/1994 | Jones | 210/755 |
| 5,395,546 | 3/1995 | Hung et al. | 252/90 |
| 5,478,482 | 12/1995 | Jones et al. | 210/753 |
| 5,498,415 | 3/1996 | Jones | 424/409 |
| 5,514,287 | 5/1996 | Jones et al. | 210/753 |

FOREIGN PATENT DOCUMENTS

WO93/04582  3/1993  WIPO .
9304987     3/1993  WIPO .

OTHER PUBLICATIONS

OxyChem Material Safety Data Sheet, Apr. 23, 1993.

Primary Examiner—John Pak
Attorney, Agent, or Firm—Woodard, Emhardt, Naughton Moriarty & McNett

[57] ABSTRACT

A slow-dissolving sanitizing and clarifying puck for use in water such as swimming pool water preferably includes about 63% to about 80% trichloro-s-triazinetrione, about 4% to about 12% sodium tetraborate, about 10% to about 22% aluminum sulfate, and about 1% to 5% glycoluril.

28 Claims, No Drawings

SLOW-DISSOLVING MULTI-FUNCTIONAL SANITIZER AND CLARIFIER

FIELD OF THE INVENTION

The present invention relates generally to chemicals for treating water such as swimming pool water, and more particularly to a slow-dissolving solid compressed product containing a sanitizer, clarifier and algicide.

BACKGROUND TO THE INVENTION

Chloroisocyanuric acids such as trichloroisocyanuric acid (also referred to as "TCCA," or by its more formal chemical name trichloro-s-triazinetrione) is effectively used as a sanitizer for recreational water systems such as swimming pools, spas, hot tubs, etc. Solid TCCA is commonly compressed into tablets or pucks that are convenient to use, and provide the benefit of dissolving slowly and uniformly in water to continuously release the sanitizer over long periods of time. TCCA is rarely compressed with other chemicals that may be oxidized or which promote the decomposition of TCCA. This is due to the safety hazard associated with compressing TCCA, a strong oxidizer, with other chemicals.

A variety of other agents such as aluminum sulfate and sodium tetraborate are also known to provide beneficial properties to water. For example, hydrated aluminum sulfate (alum) is used to clarify water due to its ability to flocculate or precipitate impurities in the water. The flocculated or precipitated impurities are normally larger than the original impurity and, as a result, the impurities are more readily removed via water filtration.

In addition, flocculants provide the additional benefit of reducing the demand on oxidizers or sanitizers in the water. The materials that are flocculated by alum and other such flocculants are commonly organic in nature. Since the flocculant helps remove these organics from the water, less oxidizer is needed. Consequently, lower oxidizer/sanitizer levels (chlorine, bromine, hydrogen peroxide, ozone, etc.) are needed to keep the water clean and safe.

Boron derivatives like borax, boric acid, etc., are also known to provide beneficial properties to water. For example, boron-containing compounds such as borax are known to provide algicidal and fungicidal properties to water when maintained at appropriate levels.

Unfortunately, both alum and borax are both highly water soluble, and the addition of water-soluble additives to trichlor is known to either increase trichlor's water dissolution rate or cause the tablets to prematurely disintegrate or collapse. This rapid dissolution of trichlor is generally undesirable and inconvenient since users are then required to add product more frequently to maintain the desired level of residual chlorine in the water.

A need therefore exists for a method of incorporating water-soluble compounds such as alum and borax into solid trichlor sanitizer pucks that do not either disintegrate or dissolve more quickly than trichlor itself. The present invention addresses that need.

SUMMARY OF THE INVENTION

Briefly describing one aspect of the present invention, there is provided a slow-dissolving solid compressed product for sanitizing and clarifying water such as swimming pool water. The solid compressed product preferably includes about 65% to about 80% by weight trichloro-s-triazinetrione, about 4% to about 12% sodium tetraborate, about 10% to about 22% aluminum sulfate, and about 1% to 5% glycoluril. Other components such as dyes, boric acid, etc., may also be included.

One object of the present invention is to provide a sanitizing, clarifying and algicidal puck that dissolves slowly in swimming pool water.

Another object of the present invention is to provide a composition and/or method to slowly release beneficial water soluble agents in combination with a sanitizer.

Further objects and advantages of the present invention will be apparent from the following description.

DESCRIPTION OF THE PREFERRED EMBODIMENT

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the illustrated embodiments, and such further applications of the principles of the invention as illustrated herein being contemplated as would normally occur to one skilled in the art to which the invention pertains.

As previously indicated, the present invention relates generally to slow-dissolving solid compressed portions of sanitizing and clarifying agents for use in water such as recreational water, toilet tanks, industrial tanks, etc. In one preferred embodiment the pucks include between about 30% and about 98% trichloro-s-triazinetrione, between about 1% and about 50% sodium tetraborate, between about 1% and about 50% aluminum sulfate, and between about 0.2% and about 15% glycoluril. More preferably, those components are present in the amounts of between about 50% and about 90% trichloro-s-triazinetrione, between about 2% and about 40% sodium tetraborate, between about 2% and about 40% aluminum sulfate, and between about 0.5% and about 7% glycoluril. In the most preferred aspects of the invention, the composition comprises between about 65% and about 80% trichloro-s-triazinetrione, between about 4% and about 12% sodium tetraborate, between about 10% and about 22% aluminum sulfate, and between about 1% and about 5% glycoluril.

As to the specific components, the trichloro-s-triazinetrione of the present invention is a staple chemical which is commercially available. In another aspect of the present invention the trichlor is optionally replaced in part or entirely with other slow dissolving halogen sanitizers like 1-bromo-3-chloro-5,5-dimethylhydantoin, 1,3-dichloro-5,5-dimethylhydantoin or other halogenated and/or alkylated hydantoins. Alternatively, other chloroisocyanuric acids such as dichloroisocyanuric acid may be used. The best mode of the invention uses trichloroisocyanuric acid however, and that chemical will used in the following description and examples. As previously indicated, the chemical is also referred to as "TCCA," or by its more formal chemical name of trichloro-s-triazinetrione, or by the abbreviated name "trichlor."

The concentration of trichlor in the total formula is generally between about 30 and 98%. Preferably trichlor is present in an amount of between about 50% and 95%; most preferably between about 65% and 80% of the total formula mass.

The aluminum sulfate (alum) of the present invention commonly is provided having any of a variety of different equivalent amounts of hydrated water. Any hydrate is acceptable for use in the invention; preferably alum having from 2 to 20 equivalents of water per mole of aluminum sulfate is used. In alternative embodiments of the invention the aluminum sulfate is a hydrated potassium alum, or hydrated sodium alum.

The aluminum sulfate concentration can be varied from 1 to 50 or preferably from 2 to 40 percent of the total formula mass. In the most preferred embodiment the aluminum sulfate is present in an amount of between about 10% and about 22% of the total composition.

The boron-containing component is preferably provided as a borax hydrate, a product which is commercially available with a variety of different equivalent amounts of hydrated water. Borax hydrates that contain from 3 to 18 equivalents of water, or preferably from 4 to 14 equivalents of water per mole of borax, are most effectively used. Additionally, the borax can be partially or totally replaced with other boron-containing compounds such as boric acid or other borax oxygen oligomers.

The sodium tetraborate (borax) concentration can be varied from 1 to 50 or preferably from 2 to 40 percent of the total formula mass. In the most preferred embodiment the borax is present in the amount of between about 4% and about 12% of the total composition.

In the preferred embodiments of the present invention glycoluril is also included in the formulation. The glycoluril may be substituted or unsubstituted, and is most preferably of the structure:

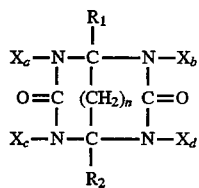

wherein $R_1$ and $R_2$ are each selected from the group consisting of hydrogen, lower alkyl groups of from 1–4 carbon atoms and phenyl; each $X_i$ is selected from the group consisting of hydrogen, chlorine and bromine; and n is either 0 or 1. As used herein, the term "glycoluril" includes all forms of glycoluril falling within the above formula. The term "unsubstituted glycoluril" refers solely to glycoluril according to the foregoing formula in which each of $R_1$, $R_2$ and $X_i$ is hydrogen.

The glycoluril is preferably included in the amount of between about 0.2 and about 15 percent. Preferably from 0.5 to 7% glycoluril is used, most preferably about 1% to about 5%.

The average glycoluril particle size is typically less than 500 microns. Dimethylhydantoin or other molecules that contain imide and amide functional groups or these molecules halogenated analogues can be used to either partially or totally replace the glycoluril. The particle sizes of the other mixture components typically are smaller than 2.0 millimeters.

The compositions of the present invention are provided as a solid compressed product, and may be of virtually any size or shape. Most preferably, the compressed product is shaped as a solid tablet, stick or puck which is easily accommodated by standard swimming pool skimmer baskets, chemical feeders or floating release devices. For other uses, such as in hot tubs, spas, toilet bowls and industrial applications, different sizes and/or shapes may be preferred.

As previously indicated, additional components such as binders, tabletting aids, mold release agents, corrosion inhibitors, scale inhibitors or dyes may be incorporated into the tablets or pucks. The selection of such components is within the capability of those skilled in the art.

Reference will now be made to specific examples using the compositions described above. It is to be understood that the examples are provided to more completely describe preferred embodiments, and that no limitation to the scope of the invention is intended thereby.

The first example is a control example to establish the dissolution rate of pucks of trichlor alone. Next, examples illustrating the preferred embodiments of the invention are provided. Finally, comparative examples demonstrating puck instability and rapid dissolution rates obtained when trichlor is formulated with either alum or borax independently are provided. These comparative examples support the conclusions of the prior art that water-soluble species would greatly increase the dissolution rate of trichlor and trichlor-based formulas.

The general procedure for all examples was as follows. Blended products were prepared by weighing the appropriate amounts of each constituent into a container, the container was then closed, placed within a "Vee-Type Blender," and tumbled for 30 minutes. The blended product was then compressed into a solid puck.

Pucks that weigh about 7 ounces (200 g) dry and have a three inch diameter were manufactured in either laboratory or commercial presses. The compression time and pressure were controlled to yield pucks that had crush strengths similar to commercial trichlor products with similar dimension and mass.

Dissolution rates were determined for test pucks. The initial puck weight was determined by immersing the dry puck in a beaker of water for 30 minutes, removing the puck from the water, gently patting the puck surface with a paper towel, and weighing the puck. The moist puck was then placed in a skimmer basket and placed in a skimmer attached to the pool. The skimmer baskets were periodically removed from the skimmers and the pucks were gently patted dry and weighed.

Puck dissolution rates were tested in a 5,000 gallon (19,000 L) pool equipped with six skimmers that are typically used in swimming pools. Flow rates through the skimmers were maintained at 30 gallons/minute (114 L/min). Flow through the skimmers was maintained for either 24 hrs/day or 10 hours/day. The pool temperature was maintained at 80° F. (26.7° C.). One puck was placed in each skimmer during the test.

EXAMPLE 1

Tests to determine the dissolution rate of pucks containing 100% trichlor were performed. In particular, two control experiments were performed—one having a 24 hour per day pump time and the other having a 10 hour per day pump time. In the 10 hour per day pump time experiment the puck was left in the water with the pump off for the remaining 14 hours per day.

The dissolution rates for the two experiments are shown below as examples 1a and 1b. These examples can be used to evaluate the dissolution rate of the blended products in the other examples. The dissolution rate is measured by the number of pump hours required to dissolve 80% of the compressed product relative to its original mass.

TABLE 1

| Test | % Trichlor | % Alum | % Borax | Pump Hours to 80% Dissolution | Pump Hours per Day |
| --- | --- | --- | --- | --- | --- |
| 1a | 100 | 0 | 0 | 38 | 24 |
| 1b | 100 | 0 | 0 | 32 | 10 |

EXAMPLE 2

Example 2 shows the most preferred embodiment of the present invention, particularly a compressed puck comprising about 73% trichlor, about 6.5% borax, about 18% alum and about 3% glycoluril.

Using the general procedure above, pucks were mixed and tabletized, and dissolution rates were determined. It can be seen by comparing Example 2 with Example 1 that the composition of the present invention has a longer (slower) dissolution time than pucks comprising trichlor alone.

TABLE 2

| Test | TCCA | Alum | Borax | Glycoluril | Boric Acid | Pump Hours to 80% Dissolution |
| --- | --- | --- | --- | --- | --- | --- |
| 2a | 72.2% | 18% | 6.5% | 3% | 0.16% | 61 |
| 2b | 72.9 | 18 | 6.6 | 3 | 0 | 61 |
| 2c | 73.2 | 18 | 6.6 | 2.5 | 0 | 60 |

EXAMPLE 3

A 3" puck was manufactured as described above from commercially available trichlor (75%) and sodium tetraborate pentahydrate (25%). The dissolution rate of this puck was determined in an identical manner as described above. The entire puck dissolved within the first 16 hours that the pump was turned on and water was flowing over the puck.

EXAMPLE 4

A 3" puck was manufactured as described above from commercially available trichlor (75%) and hydrated aluminum sulfate (25%). The dissolution rate of this puck was determined as described above in the general procedure. The puck crumbled and collapsed within the first 30 minutes that the puck was placed in standing water.

While the invention has been illustrated and described in detail in the foregoing description, the same is to be considered as illustrative and not restrictive in character, it being understood that only the preferred embodiment has been shown and described and that all changes and modifications that come within the spirit of the invention are desired to be protected.

We claim:

1. A solid, compressed sanitizing and clarifying product for use in water, consisting essentially of:
   (a) about 30% to about 98% trichloro-s-triazinetrione;
   (b) about 1% to about 50% sodium tetraborate
   (c) about 1% to about 50% aluminum sulfate; and
   (d) about 0.2% to about 15% glycoluril.

2. The sanitizing and clarifying product of claim 1 wherein about 50% to about 95% trichloro-s-triazinetrione is present in the product.

3. The sanitizing and clarifying product of claim 2 wherein about 65% to about 80% trichloro-s-triazinetrione is present in the product.

4. The sanitizing and clarifying product of claim 1 wherein about 2% to about 40% sodium tetraborate is present in the product.

5. The sanitizing and clarifying product of claim 4 wherein about 4% to about 12% sodium tetraborate is present in the product.

6. The sanitizing and clarifying product of claim 1 wherein about 2% to about 40% aluminum sulfate is present in the product.

7. The sanitizing and clarifying product of claim 6 wherein about 10% to about 22% aluminum sulfate is present in the product.

8. The sanitizing and clarifying product of claim 1 wherein about 0.05% to about 7% glycoluril is present in the product.

9. The sanitizing and clarifying product of claim 8 wherein about 1% to about 5% glycoluril is present in the product.

10. The sanitizing and clarifying product of claim 1 wherein the product consists essentially of:
    (a) about 70% to about 75% trichloro-s-triazinetrione;
    (b) about 5% to about 10% sodium tetraborate;
    (c) about 15% to about 20% aluminum sulfate; and
    (d) about 3% glycoluril.

11. The sanitizing and clarifying product of claim 1 wherein the product contains a dye.

12. A solid, compressed santizing and clarifying product for use in water, consisting essentially of:
    (a) about 30% to about 98% trichloro-s-triazinetrione;
    (b) about 1% to about 50% sodium tetraborate;
    (c) about 1% to about 50% aluminum sulfate;
    (d) about 0.2% to about 15% glycoluril; and
    (e) boric acid.

13. A method of simultaneously sanitizing and clarifying water, the method comprising adding to the water a slow-dissolving solid compressed sanitizing and clarifying product consisting essentially of:
    (a) about 30% to about 98% trichloro-s-triazinetrione;
    (b) about 1% to about 50% sodium tetraborate;
    (c) about 1% to about 50% aluminum sulfate; and
    (d) about 0.2% to about 15% glycoluril.

14. The method of claim 13 wherein 50% to about 95% trichloro-s-triazinetrione is present in the sanitizing and clarifying product.

15. The method of claim 14 wherein 65% to about 80% trichloro-s-triazinetrione is present in the sanitizing and clarifying product.

16. The method of claim 13 wherein 2% to about 40% sodium tetraborate is present in the sanitizing and clarifying product.

17. The method of claim 16 wherein 4% to about 12% sodium tetraborate is present in the sanitizing and clarifying product.

18. The method of claim 13 wherein 2% to about 40% aluminum sulfate is present in the sanitizing and clarifying product.

19. The method of claim 18 wherein 10% to about 22% aluminum sulfate is present in the sanitizing and clarifying product.

20. The method of claim 13 wherein 0.5% to about 7% glycoluril is present in the sanitizing and clarifying product.

21. The method of claim 20 wherein 1% to about 5% glycoluril is present in the sanitizing and clarifying product.

22. The method of claim 13 wherein the sanitizing and clarifying product consists essentially of:
    (a) about 70% to about 75% trichloro-s-triazinetrione;
    (b) about 5% to about 10% sodium tetraborate;

(c) about 15% to about 20% aluminum sulfate; and (d) about 2.5% glycoluril.

23. The method of claim 13 wherein the sanitizing and clarifying product contains a dye.

24. A method of simultaneously sanitizing and clarifying water, the method comprising adding to the water a slow-dissolving solid compressed product consisting essentially of:

(a) about 30% to about 98% trichloro-s-triazinetrione;

(b) about 1% to about 50% sodium tetraborate;

(c) about 1% to about 50% aluminum sulfate;

(d) about 0.2% to about 15% glycoluril; and (e) boric acid.

25. A solid, compressed sanitizing and clarifying product for use in water, consisting essentially of:

(a) about 30% to about 98% of a halogen-containing sanitizer compound;

(b) about 1% to about 50% of a tetraborate compound;

(c) about 1% to about 50% aluminum sulfate; and (d) about 0.2% to about 15% glycoluril.

26. The sanitizing and clarifying product of claim 25 wherein the halogen-containing sanitizer compound is a chloroisocyanuric acid.

27. The sanitizing and clarifying product of claim 25 wherein the halogen-containing sanitizer compound is a dimethylhydantoin.

28. The sanitizing and clarifying product of claim 27 wherein the dimethylhydantoin is a 1-bromo-3-chloro-5,5-dimethylhydantoin or 1,3-dichloro-5,5-dimethylhydantoin.

* * * * *

UNITED STATES PATENT AND TRADEMARK OFFICE
CERTIFICATE OF CORRECTION

PATENT NO. : 5,648,314

DATED : July 15, 1997

INVENTOR(S) : Thomas M. Lachocki et al.

It is certified that error appears in the above-identified patent and that said Letters Patent is hereby corrected as shown below:

Abstract: title page, line 3, please change "63%" to --65%--.

In col. 4, line 2, please change "ark" to --art--.

Signed and Sealed this

Ninth Day of December, 1997

Attest:

BRUCE LEHMAN

Attesting Officer

Commissioner of Patents and Trademarks